United States Patent [19]
Pelosi, Jr.

[11] 3,980,689
[45] Sept. 14, 1976

[54] N-(2,5-DICHLORO-4-THIOCYANATOPHENYL)-β-ALANINE

[75] Inventor: Stanford S. Pelosi, Jr., Norwich, N.Y.

[73] Assignee: Morton-Norwich Products, Inc., Norwich, N.Y.

[22] Filed: Dec. 3, 1975

[21] Appl. No.: 637,164

[52] U.S. Cl. .................................. 260/454; 424/302
[51] Int. Cl.² ........................................ C07C 161/03
[58] Field of Search .................................. 260/454

[56] References Cited
UNITED STATES PATENTS

| | | | |
|---|---|---|---|
| 3,202,690 | 8/1965 | Previc | 260/454 |
| 3,285,730 | 11/1966 | Weis et al. | 260/454 |
| 3,384,472 | 5/1968 | Mussell et al. | 260/454 |
| 3,421,880 | 1/1969 | Mussell et al. | 260/454 |

OTHER PUBLICATIONS

Wiley; "Organic Reactions" 3, pp. 250–266, (1946).

Primary Examiner—Lewis Gotts
Assistant Examiner—D. R. Phillips
Attorney, Agent, or Firm—Anthony J. Franze

[57] ABSTRACT

N-(2,5-Dichloro-4-thiocyanatophenyl)-β-alanine is an effective antifungal agent.

1 Claim, No Drawings

N-(2,5-DICHLORO-4-THIOCYANATOPHENYL)-β-ALANINE

This invention relates to the compound N-(2,5-dichloro-4-thiocyanatophenyl)-β-alanine of the formula:

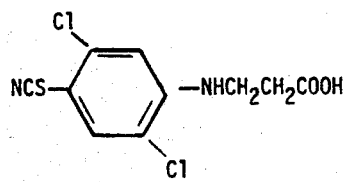

This compound possesses antifungal activity and is useful in the prevention of fungal growth. When dissolved in 50 percent ethanol at a concentration of 985 mcg/ml, it inhibits the growth of *Microsporum canis* in the commonly employed agar cup plate test for fungistatic activity. At a concentration of 250 mcg/ml in dimethylformamide, it inhibits the growth of *Aspergillus niger* in nutrient agar seeded therewith. This compound can be combined in known fashion with various compatible excipients and adjuvants to provide antifungal compositions.

The compound of this invention is readily prepared by reacting N-(2,5-dichlorophenyl)-β-alanine with sodium thiocyanate in the presence of bromine dissolved in acetic acid. In order that this invention may be readily available to and understood by those skilled in the art, the method now preferred for making it is described:

A solution of 6 ml (0.11 mole) of bromine in 20 ml of acetic acid was added dropwise over 20 min to a stirred mixture of 25 g (0.10 mole) of N-(2,5-dichlorophcyl)-β-alanine, 20.5 g (0.25 mole) of sodium thiocyanate and 100 ml of acetic acid at 15°–20°. An additional 80 ml of acetic acid was added to facilitate stirring which was continued for 1 hr. The reaction mixture was poured into 600 ml of cold water. The yellow solid was collected by filtration, washed with water and dried in an oven at 100° for 2 hrs to give 30 g (100%) of N-(2,5-dichloro-4-thiocyanatophenyl)-β-alanine. Two recrystallizations from $CH_3NO_2$ gave an analytical sample, m.p. 133°–135°.

Anal. Calcd. for $C_{10}H_8Cl_2OS$: C, 41.25; H, 2.77; N, 9.62. Found: C, 40.97; H, 2.84, N, 9.63.

What is claimed is:
1. The compound N-(2,5-dichloro-4-thiocyanatophenyl)-β-alanine.

\* \* \* \* \*